United States Patent
Griesdorf et al.

(10) Patent No.: US 9,097,655 B2
(45) Date of Patent: Aug. 4, 2015

(54) PROGRAMMABLE GAIN AMPLIFIER WITH MULTI-RANGE OPERATION FOR USE IN BODY SENSOR INTERFACE APPLICATIONS

(75) Inventors: Dustin Griesdorf, Waterloo (CA);
Jacob Nielsen, Waterloo (CA);
Volodymyr Yavorskyy, Waterloo (CA)

(73) Assignee: SEMICONDUCTOR COMPONENTS INDUSTRIES, LLC, Phoenix, AZ (US)

( * ) Notice: Subject to any disclaimer, the term of this patent is extended or adjusted under 35 U.S.C. 154(b) by 433 days.

(21) Appl. No.: 13/228,274

(22) Filed: Sep. 8, 2011

(65) Prior Publication Data
US 2012/0235739 A1     Sep. 20, 2012

Related U.S. Application Data

(60) Provisional application No. 61/381,468, filed on Sep. 10, 2010.

(51) Int. Cl.
*G01N 27/403* (2006.01)
*G01N 27/327* (2006.01)
*A61B 5/145* (2006.01)

(52) U.S. Cl.
CPC ........ *G01N 27/3273* (2013.01); *A61B 5/14532* (2013.01)

(58) Field of Classification Search
CPC . G01N 33/5438; G01N 27/403; G01N 27/00; B01J 19/0046; B01J 2219/00527; B01J 2219/00585; H03G 3/3042; H03G 3/3047; H03G 3/3036; H03G 3/001; H03G 3/3052
USPC .......................................... 436/149; 330/129
See application file for complete search history.

(56) References Cited

U.S. PATENT DOCUMENTS

| | | | |
|---|---|---|---|
| 2003/0147428 A1* | 8/2003 | Bonthron et al. ............. | 370/533 |
| 2008/0012637 A1* | 1/2008 | Aridas et al. .................. | 330/129 |
| 2009/0120810 A1* | 5/2009 | Phan et al. .................... | 205/792 |
| 2011/0208435 A1* | 8/2011 | Elder et al. ...................... | 702/19 |

OTHER PUBLICATIONS

A Programmable 0.18-um CMOS Electrochemical Sensor Microarray for Biomolecular Detection Arjang Hassibi and Thomas H. Lee IEEE Sensors Journal, vol. 6, No. 6, Dec. 2006.*

* cited by examiner

*Primary Examiner* — Krishnan S Menon
*Assistant Examiner* — Dwan A Gerido
(74) *Attorney, Agent, or Firm* — Robert F. Hightower (57) ABSTRACT

A system for analyte measurement includes a programmable gain amplifier including a first input terminal operatively coupling to the output of a sensor for sensing an analyte, a second input terminal operatively coupling to a voltage source, and an output terminal for providing an output based on a difference between inputs on the first input terminal and the second input terminal A controller is operatively coupled to the programmable gain amplifier for configuring the operation range of the programmable gain amplifier and/or selecting the output of the programmable gain amplifier for analyte measurement. The method includes monitoring an output from a programmable gain amplifier operatively coupling to a sensor for sensing an analyte, and controlling the operation range of the programmable gain amplifier, and/or selecting the output of the programmable gain amplifier for analyte measurement.

20 Claims, 5 Drawing Sheets

PROGRAMMABLE GAIN AMPLIFIER WITH MULTI-RANGE OPERATION FOR USE IN BODY SENSOR INTERFACE APPLICATIONS

BACKGROUND

1. Field

The disclosed embodiments relate to a system and method for processing sensor data, and more specifically to a system and method for analyte measurement.

2. Brief Description of Related Developments

A blood glucose meter is used by individuals to measure the concentration of glucose in their blood. People with diabetes have a special interest in measuring the concentration of glucose as the level of glucose can be an indication of whether treatment of their diabetes is required or not.

Handheld, commercially available blood glucose meters are typically used for this purpose. Such commercially available meters work by having the patient place a small blood drop on a test strip (a "sensor"). Then the test strip is inserted in the glucose meter followed by processing of the test strip in the glucose meter to determine the concentration of the glucose. The processing is typically done by a processing engine that may be composed of an electro-chemical sensor interface and a controller.

In operation, the sensor will typically produce a small current (known as "work current") when biased with a voltage via an operational amplifier configured as a transimpedance amplifier. The current will vary as function of the chemical reaction happening in the test strip and the voltage output of the transimpedance amplifier will vary accordingly. There is a need to provide, based on the work current, an accurate representation of the concentration of glucose.

SUMMARY

The method and system of the disclosed embodiments obviate or mitigate at least one of the disadvantages of existing systems.

According to an aspect of the disclosure, there is provided a system for analyte measurement, which includes: at least one programmable gain including a first input terminal operatively coupling to an output of a sensor for sensing an analyte, a second input terminal operatively coupling to a voltage source, and an output terminal for providing an output based on a difference between first and second inputs on the first input terminal and the second input terminal; and a controller operatively coupling to at least one programmable gain amplifier, for configuring the operation range of the at least one programmable gain amplifier and/or selecting the output of the at least one programmable gain amplifier for analyte measurement.

According to an aspect of the disclosure, there is provided a method for analyte measurement, which includes: monitoring an output from at least one programmable gain amplifier, at least one programmable gain amplifier including a first input terminal operatively coupling to an output of a sensor for sensing an analyte, a second input terminal operatively coupling to a voltage source, and an output terminal for providing an output based on a difference between first and second inputs on the first input terminal and the second input terminal; and controlling the operation range of the at least one programmable gain amplifier, and/or selecting the output of the at least one programmable gain amplifier for analyte measurement.

BRIEF DESCRIPTION OF THE DRAWINGS

These and other aspects of the disclosed embodiments will become more apparent from the following description in which reference is made to the appended drawings wherein.

DETAILED DESCRIPTION

The embodiments are described in detail using a meter for measuring analyte, such as a glucose meter for measuring the concentration of glucose in blood; however, this does not exclude the possibility of measuring the level of any other analyte. It would be appreciated by one of ordinary skill in the art that the term "analyte" represents, without limitation, to a substance or chemical constituent in a physiological fluid, such as blood, urine, spinal fluid, lymph fluid, which can be analyzed.

Figure 1:
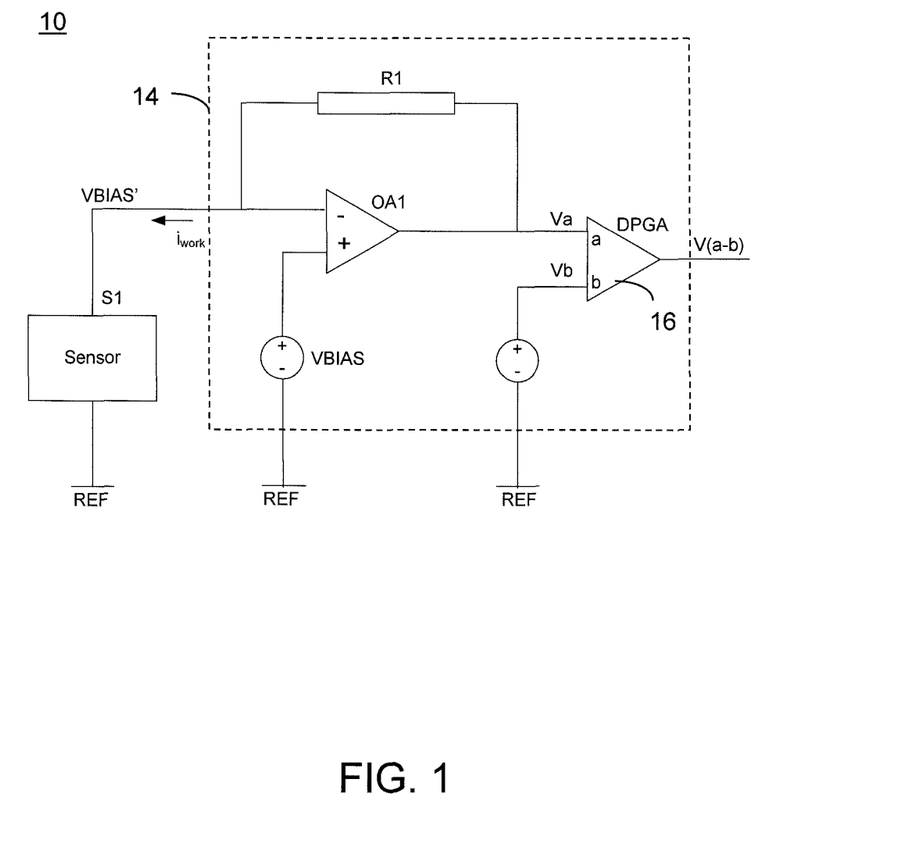
FIG. 1 illustrates an example of a measuring/sensor system including a sensor interface having a digitally programmable gain amplifier (DPGA)

Referring to FIG. 1, there is illustrated an example of a measuring/sensor system 10 having an electro-chemical sensor S1 and a sensor interface 14. The sensor interface 14 is operatively connected to the sensor S1 to interfere with the measurement of an analyte of interest in the sensor S1. In this example, the sensor interface 14 forms a glucose meter. The system 10 may assess the glucose level in a drop of blood placed on the sensor S1. It would be appreciated by one of ordinary skill in the art that the sensor interface 14 may be in a handheld device for glucose measurement, and the sensor S1 may form a test strip which is detachably coupled to the sensor interface 14. The sensor interface 14 may form a processing engine (e.g., 20 of FIG. 3) with a controller (e.g., 18 of FIG. 3).

It would be appreciated by one of ordinary skill in the art that other components not shown in the drawings may exist in the system 10. Other components such as one or more A/D converters, more operational amplifiers, reference voltages, battery components may exist in the system 10 or the sensor interface 14.

The sensor S1 is connected between a bias voltage VBIAS' and a reference voltage REF. The reference voltage REF may be, for example, but not limited to, GND (ground).

The sensor interface 14 includes a transimpedance amplifier for converting a current generated by a chemical reaction on the sensor S1 into a voltage. The transimpedance amplifier in the sensor interface 14 includes an operational amplifier (opamp) OA1 and a passive circuit element R1. The opamp OA1 may be selected so that it has characteristics suitable for the purpose of measuring work currents.

In FIG. 1, one opamp OA1 is illustrated. It would be appreciated by one of ordinary skill in the art that the sensor interface 14 may include more than one opamp. In FIG. 1, one passive circuit element R1 is illustrated. It would be appreciated by one of ordinary skill in the art that the sensor interface 14 may include more than one passive circuit element disposed in parallel.

The opamp OA1 has a positive input terminal and a negative input terminal. A bias voltage VBIAS is applied to the positive terminal of the opamp OA1. The voltage VBIAS is typically generated by a reference voltage circuitry or a derivative thereof, which includes a reference voltage supply REF. In one example, VBIAS is substantially equal to VBIAS'.

The passive circuit element R1 is operatively connected to the negative input terminal of the opamp OA1 and the output Va of the opamp OA1. The passive circuit element R1 is, for example, a feedback resistor. It would be appreciated by one of ordinary skill in the art that the sensor interface 14 may include more than one passive circuit element configured in parallel to one opamp. One of passive circuit elements may be selectively connected to the input terminal of the opamp OA1 and the output Va of the opamp OA1. It would be appreciated by one of ordinary skill in the art that the passive circuit element R1 is not limited to the resistor, and may be another element, such as a capacitor or a memristor or a combination of the resistor and the capacitor and the memristor. It would be appreciated by one of ordinary skill in the art that the passive circuit element R1 may be an active circuit element emulating a passive circuit element.

The sensor interface 14 further includes a differential programmable gain amplifier (DPGA) 16. In FIG. 1, one DPGA 16 is illustrated. It would be appreciated by one of ordinary skill in the art that the sensor interface 14 may include more than one DPGA 16, which may operate in parallel to the same input signals. The transimpedance amplifier (or the opamp OA1) and the DPGA 16 may be integrated on one chip. The transimpedance amplifier (or the opamp OA1) and the DPGA 16 may form a processing engine.

The DPGA 16 has a first input terminal "a" and a second input terminal "b". The output Va of the opamp OA1 constitutes an input to the first input terminal "a" of the DPGA 16. A voltage source Vb is applied to the second input terminal "b" of the DPGA 16. Vb may be generated by a reference voltage circuitry or a derivative hereof. Vb may be, for example, but not limited to, equal to VBIAS. The DPGA 16 provides an output V(a−b) based on the difference voltage between voltages Va and Vb or an amplified version of the difference. Other inputs to the DPGA 16 than the ones described are also applicable to the system 10.

Figure 2:
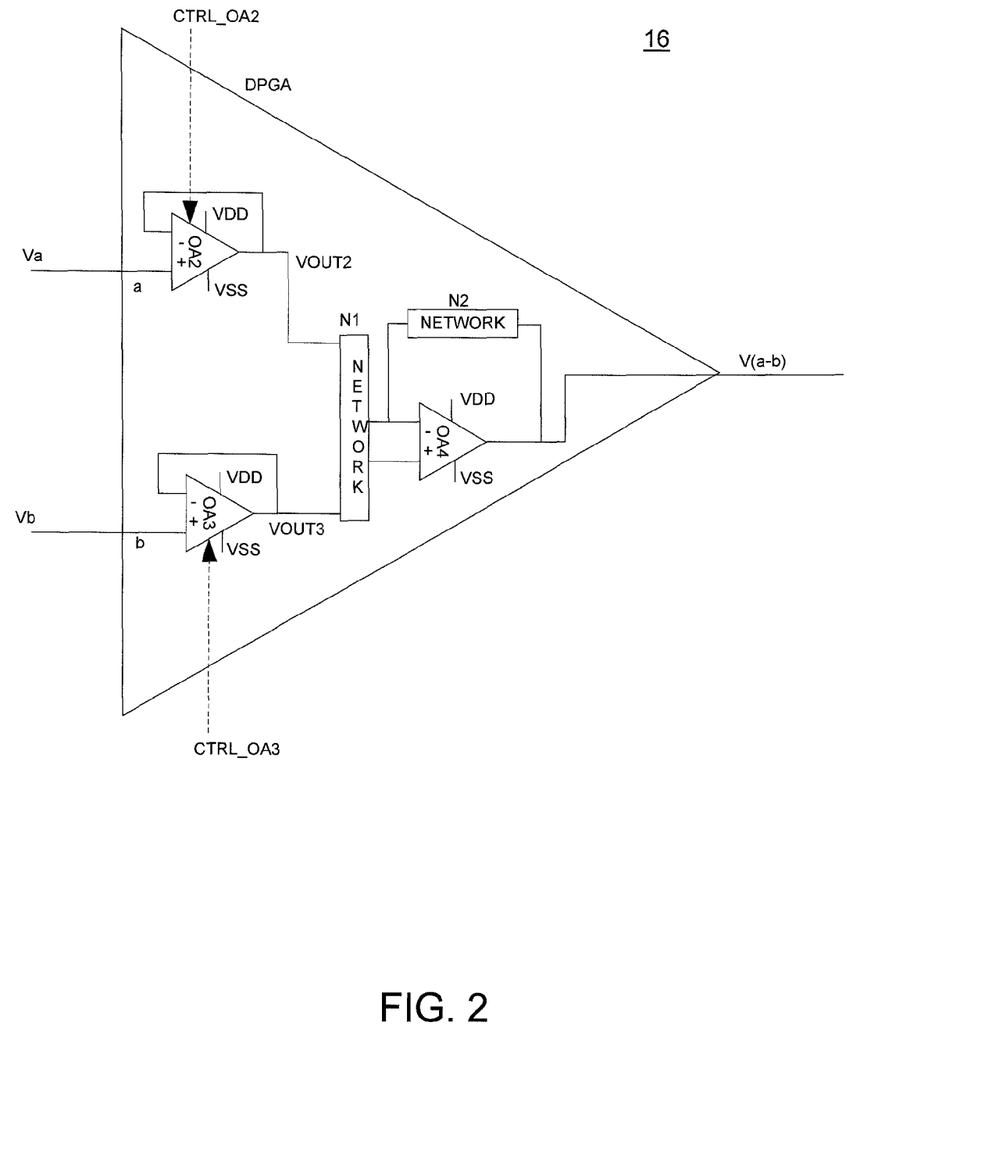
FIG. 2 illustrates components of the DPGA shown in FIG. 1.

Referring to FIG. 2, there is illustrated one example of the DPGA 16. The DPGA 16 includes buffer operational amplifiers (buffer opamps) OA2 and OA3, and an opamp OA4. Each of the buffer amplifiers OA2 and OA3 and the opamp OA4 includes a negative input terminal and a positive input terminal. Each of the buffer opamps OA2 and OA3 and the opamp OA4 is operatively connected to power supply rails VDD and VSS. VDD is, for example, but not limited to, a positive supply voltage, and VSS is, for example, but not limited to, connected to ground. It will be appreciated by one of ordinary skill in the art that power supply schemes other than the positive supply voltage and the ground voltage may exist for VDD and VSS.

The positive input terminal of the buffer opamp OA2 is operatively connected to the first input voltage Va of the DPGA 16. The negative input terminal of the buffer opamp OA2 is operatively connected to the output VOUT2 of the buffer opamp OA2. The positive input terminal of the buffer amplifier OA3 is operatively connected to the second input voltage Vb of the DPGA 16. The negative input terminal of the buffer opamp OA3 is operatively connected to the output VOUT3 of the buffer opamp OA3.

The opamp OA2 is programmable to linearly operate, depending on its control signal CTRL_OA2. The opamp OA3 is programmable to linearly operate, depending on its control signal CTRL_OA3.

The outputs VOUT2 and VOUT 3 of the buffer amplifiers OA2 and OA3 are coupled to the negative and positive input terminals of the opamp OA4 via a network N1. The negative input terminal of the opamp OA4 is further coupled to its output and the output V(a−b) of the DPGA16 via a network N2. The outputs of the two amplifiers OA2 and OA3 are subtracted by the opamp OA4 and gain is applied. The networks N1 and N2 are typically used to set gain but may also have impact on the linearity of the opamp OA2, OA3, OA4 or combinations thereof. The networks N1 and N2 may be configured to adjust the operation of the opamp OA2, OA3, OA4 or combinations thereof.

In one example, the networks N1 and N2 are passive elements for generating gain. The networks N1 and N2 may be, for example, but not limited to, resistors, capacitors, or combinations thereof. It would be appreciated by one of ordinary skill in the art that the network may be an active circuit element emulating a passive circuit element. At least one of the networks N1 and N2 may include more than one passive elements that may be selectively coupled to the corresponding opamp.

The dynamic range of the first and the second input of the DPGA may be large, causing either of the two buffers or the opamp used for the differential measurement to operate in a region where they become non-linear. Operation in a non-linear region will cause the output voltage of the DPGA to be an inaccurate representation of the concentration of glucose, resulting in that the level of glucose reported back to the patient may be wrong. According to the embodiment of the system 10, the operating region of the DPGA 16 is programmable to ensure that the DPGA 16 always operates in a linear region and thus the system 10 can measure the concentration of glucose accurately.

In addition, according to the embodiment of the system 10, single supply operation of the DPGA simplifies the DPGA design and reduces the current consumption of the DPGA. Low current consumptions can extend battery life of the device.

Figure 3:
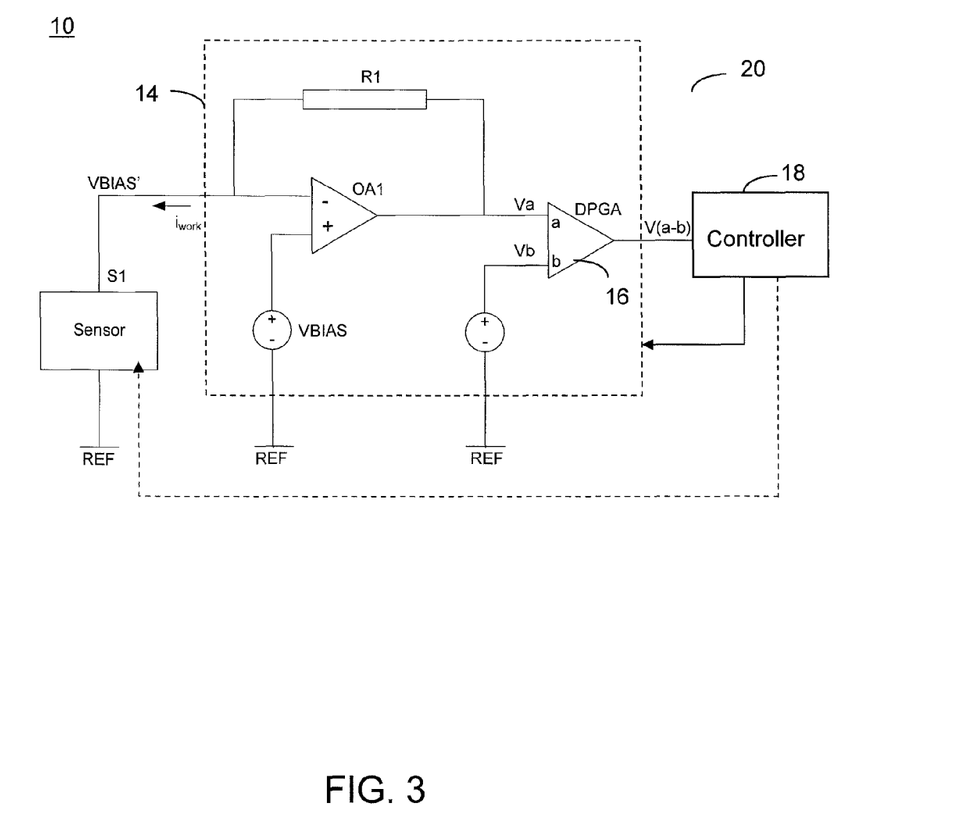
FIG. 3 illustrates a controller operatively coupling to the sensor interface of FIG. 1.

Referring to FIG. 3, there is illustrated a controller 18 operatively coupling to the output V(a−b) of the DPGA 16. The controller 18 controls at least one of the control signals CTRL_OA2 and CTRL_OA3 that controls at least one of buffers in the DPGA 16 (i.e., OA2 and OA3 of FIG. 2). The controller 18 may be, for example, a microcontroller or a digital signal processor. In the description below, "controller 18" and "microcontroller 18" may be used interchangeably. The sensor interface 14 and the controller 18 may form a processing engine 20 for a glucose meter. The controller 18 may also be operatively coupled to the output of the opamp OA1 and/or the sensor S1.

It would be appreciated by one of ordinary skill in the art that other components not shown in FIG. 3 may exist in the processing engine 20. The output V(a−b) of the DPGA 16 may be sampled in an analog-to-digital converter (ADC) before it enters the controller 18. The ADC for sampling V(a−b) may be included in the controller 18.

The controller 18 includes a repository for storing enough information about the input common mode voltage of each opamp to adequately select the operating region of the opamp and ensure that the opamp will always operate linearly no matter what the level of its input voltage (Va, Vb) is.

Referring to FIGS. 1-4, operation of the DPGA 16 is described in detail. The operation of each of the buffer opamps OA2 and OA3 is described using the buffer opamp OA2 as an example. However, the same operation applies for the buffer opamp OA3.

Typically an opamp can be designed to operate single-ended or rail-to-rail. A single-ended, low-operating region opamp typically has linear operation in the range from ~VSS to (VDD−Δ) where Δ is difference between the opamp supply voltage VDD and the maximum input common mode voltage where the opamp operates linearly. If the input common mode voltage exceeds the (VDD−Δ) threshold the opamp can saturate or exhibit other non-linear behavior. Within the input common mode voltage range where the opamp operates linearly the offset voltage of the opamp is typically constant.

Similarly, a single-ended, high-operating region opamp operates linearly in the range from (VSS+Δ) to VDD where Δ is the difference between the opamp supply voltage VSS (e.g. ground) and the minimum input common mode voltage where the opamp operates linearly. If the input common mode voltage drops below the (VSS+Δ) threshold the opamp can saturate or exhibit other non-linear behavior. Within the input common mode voltage range where the opamp operates linearly the offset voltage of the opamp is typically constant.

A rail-to-rail opamp operates from ~VSS to ~VDD; however, the operation is typically not linear across the entire range. As the input common mode voltage is swept from ~VSS to ~VDD the output offset can vary significantly. Techniques exist (such as choppering) to limit these offset variations; however, the linearity obtained via the application of such techniques may be considered inadequate for sensor interfaces for analyte measurement and these schemes may increase both the complexity and the current consumption.

The controller 18 controls CTRL_OA2 so that the opamp OA2 operates in a single-ended, low-operating region or a single-ended, high-operating region. The opamp OA2 is configured to act as a single-ended, low-operating region opamp or a single-ended, high-operating region opamp, depending on CTRL_OA2. In a further example, based on CTRL_OA2, the opamp OA2 may be configured to act as a single-ended, low-operating region opamp, a single-ended, high-operating region opamp or a rail-to-rail opamp.

Figure 4:
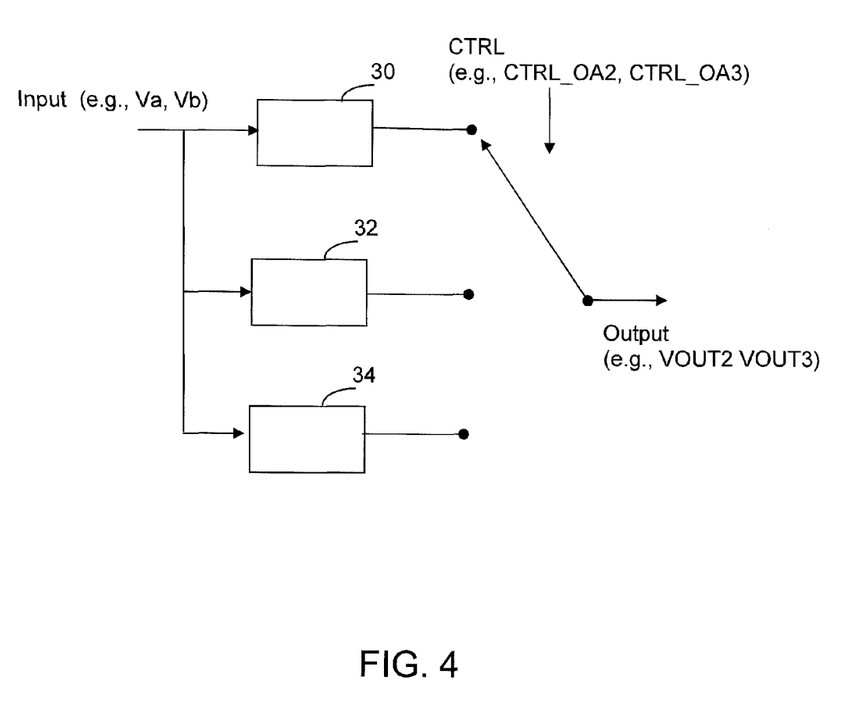
FIG. 4 illustrates one example of an operational amplifier in the DPGA of FIG. 2.

OA2 may be an opamp with a plurality of circuitries inside it, each having a different linear operation region, as shown in FIG. 4. In FIG. 4, the opamp OA2 includes three circuitries 30, 32 and 34. The control signal CTRL would select which of the three circuitries 30, 32 and 34 to use. The circuitries 30, 32 and 34 have different linear operation regions. For example, one of the circuitries 30, 32 and 34 is configured to make the opamp OA2 act as a single-ended, low-operating region opamp while the other circuitry make the opamp O2 act as a single-ended, high-operating region opamp. The third circuitry make the opamp OA2 act as a rail-to-rail opamp. One of the circuitries 30, 32 and 34 may be selected by CTRL and coupled to the output of the opamp OA2. The configuration of OA2 is not limited to that shown in FIG. 4. OA2 may have more than three circuitries, each having a different linear operation region. OA2 may have two circuitries (e.g., 30 and 32, 32 and 34, or 30 and 34), each having a different linear operation region. The same principle applies to the opamp OA3. The controller 18 shown in FIG. 3 monitors V(a−b). Typically a range of V(a−b) will be known before an analyte measurement is initiated, and the signal CTRL (CTRL_OA2, CTRL_OA3 of FIG. 2) will be set accordingly. Those control signals can also be set dynamically, i.e., if V(a−b) gets large the control signal CTRL can be changed to change the common mode operating region.

Figure 5:
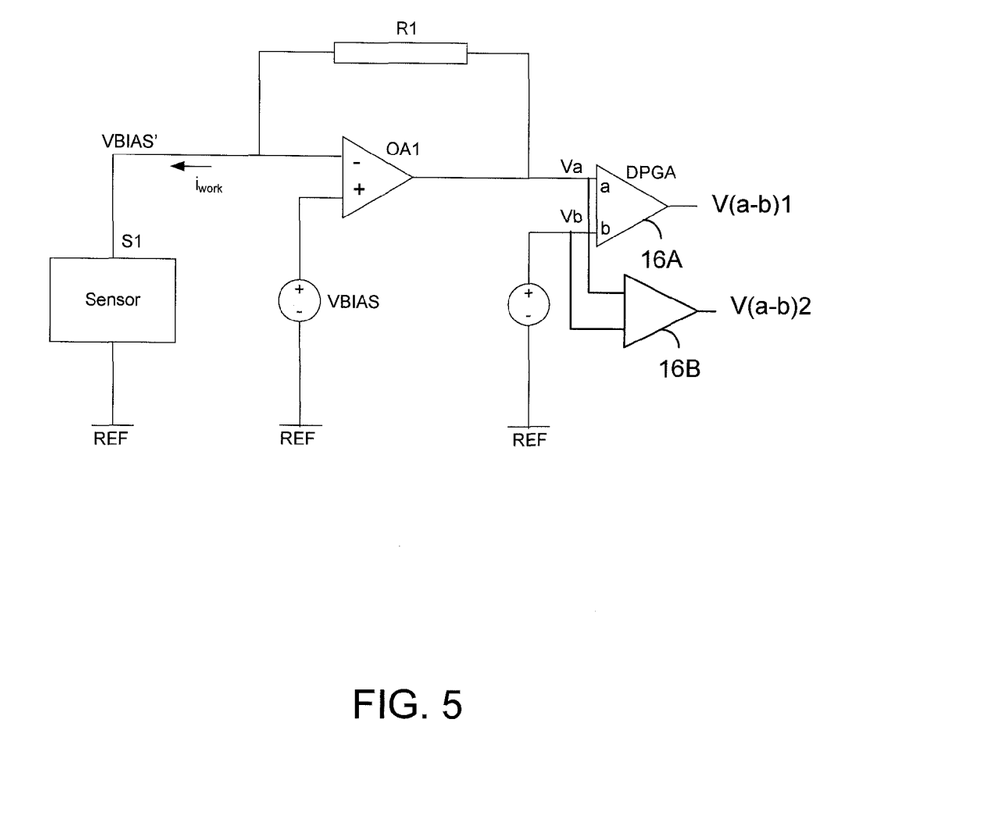
FIG. 5 illustrates a further example of a measuring/sensor system including a sensor interface having a plurality of DPGAs.

In the above disclosure, the system 10 of FIG. 1 contains one DPGA. In another example, a plurality of DPGAs may operate in parallel on the same input signals (a multi-DPGA scheme), as shown in FIG. 5. In FIG. 5, two DPGAs 16A and 16B are shown. It would be appreciated by one of ordinary skill in the art that the sensor interface may include more than two DPGAs.

Each of DPGAs 16A and 16B is coupling to Va and Vb. DPGAs 16A and 16Bs are programmable so that each can be in its selected linear operation region. Each of DPGAs 16A and 16Bs may be the same as DPGA 16 of FIG. 2. The microcontroller 18 (FIG. 3) monitors at least one of outputs V(a−b)1 and V(a−b)2 from DPGAs 16A and 16B.

In one example, one DPGA 16A may be configured to operate in a single-ended, low-operating region, and the second DPGA 16B may be configured to operate in a single-ended, high-operating region or one or both may be configured to operate rail-to-rail. The microcontroller 18 simultaneously monitors the outputs V(a−b)1 and V(a−b)2 of the two DPGAs 16A and 16B of which at least one output will always represent linear operation of the DPGA. One of V(a−b)1 and V(a−b)2 may be selected by the controller 18 as the output of the sensor interface.

The controller 18 may configure each of DPGAs as described above, for example, by monitoring the outputs of the DPGAs. Each DPGA may include a plurality of circuits, each operating in a different linear region and being selected, as shown in FIG. 4.

One or more currently preferred embodiments have been described by way of example. It will be apparent to persons skilled in the art that a number of variations and modifications can be made without departing from the scope of the invention as defined in the claims.

What is claimed is:

1. A system for analyte measurement, comprising:
    a transimpedance amplifier including a first input terminal configured for operatively coupling to an output of a sensor for sensing an analyte, a second input terminal coupled to a voltage source, and an output terminal that provides an output based on a difference between first and second inputs on the first input terminal and the second input terminal;
    a differential programmable gain amplifier (DPGA) having a first input terminal coupled to the output of the output terminal of the transimpedance amplifier and a second input terminal coupled to a reference voltage source and that provides an output based on a difference between the first and second input terminals of the DPGA, the DPGA including first and second programmable buffers with each of the first and second terminals of the DPGA coupled to an output of a respective one of the first and second programmable buffers wherein the first and second programmable buffers each have a plurality of selectable operation ranges where each selectable operation range has a different linearity region and wherein at least one operation range of the plurality of selectable operation ranges is selected responsive to a control signal; and
    a controller operatively coupled to the DPGA, wherein the controller forms a state of the control signal responsively to an input common mode voltage of each of the first and second programmable buffers, the control signal coupled between the controller and the first and second programmable buffers.

2. A system as claimed in claim 1, wherein the controller provides the control signal to each of the programmable buffers dynamically.

3. A system as claimed in claim 1, wherein the controller selects the operation range prior to testing the analyte.

4. A system as claimed in claim 1, wherein the operation ranges of the programmable buffers include one of a rail-to-rail operational region or at least a single-ended first-operating region operational region and a single-ended second-operating region operational region.

5. A system as claimed in claim 1 wherein the operation range of the plurality of operation ranges is selected responsively to a value of the output of the differential programmable gain amplifier.

6. A system as claimed in claim 1, wherein the programmable buffers are operational amplifiers including a plurality of circuitries, each circuitry having a different linear operation region that is selectable by the control signal provided to each respective programmable buffer.

7. A system as claimed in claim 1, wherein the controller monitors the output of the DPGA and provides the control signal based on information in a repository about each respective programmable buffer to ensure linear operation of each respective programmable buffer.

8. A system as claimed in claim 1, wherein a bias voltage from the voltage source coupled to the second terminal of the transimpedance amplifier is the bias voltage provided to the second input of the DPGA.

9. A system as claimed in claim 1, wherein the DPGA is a first DPGA, the system further comprises at least one additional DPGA having a first input terminal coupled to the output of the transimpedance amplifier and a second terminal coupled to the reference voltage source and wherein the at least one additional DPGA includes a different linear operation region from the first DPGA.

10. A system as claimed in claim 1, wherein the DPGA comprises:
at least one first gain network, and an additional operational amplifier having a first input terminal and a second input terminal, the output of the first programmable buffer coupled to the first input terminal of the additional operational amplifier through the at least one first gain network and the output of the second programmable buffer coupled to the second input of the additional operational amplifier via the at least one first gain network; and
at least one second gain network operatively coupled to the output of the additional operational amplifier and to the first input terminal of the additional operational amplifier.

11. A system as claimed in claim 1, wherein the system is a glucose monitoring system.

12. A method of forming a system for analyte measurement, comprising:
coupling an output of a transimpedance amplifier to a differential programmable gain amplifier (DPGA), the transimpedance amplifier having a first input terminal for operatively coupling to an output sensor for sensing an analyte and a second input terminal coupled to a voltage supply;
coupling a controller to monitor an output of the DPGA, the DPGA having a first input terminal coupled to the output of the transimpedance amplifier and a second input terminal coupled to a reference supply voltage and being selectively operable between a plurality of discrete operation ranges responsive to a control signal; and
configuring the system to control a gain range of the programmable gain of the DPGA based on the output of the DGPA.

13. A method as claimed in claim 12, further including operatively coupling an output of a programmable buffer to one of the first input terminal or the second input terminal of the DPGA, the programmable buffer including a plurality of circuitries, each circuitry having a different linear operation region, and wherein the step of configuring the system to control the operation range includes configuring the system to dynamically select one or more of the circuitries of the plurality of circuitries responsively to a value of the output of the DPGA to operate the programmable buffer in linear operation.

14. A method as claimed in claim 12, wherein configuring the system to control the operation range includes dynamically controlling the operational range.

15. A method as claimed in claim 12, including forming at least one additional DPGA disposed in parallel with the DPGA and having a first input terminal operatively coupled to the output of the transimpedance amplifier and a second input terminal operatively coupled to the reference voltage source, and
wherein configuring the system to control the operation range includes configuring the system to at least one of:
monitor the output of each DPGA for analyte measurement;
select the output of each DPGA for analyte measurement; and
selectively configure the operation range of each DPGA.

16. A method as claimed in claim 12, further including forming the DPGA to include a programmable buffer coupled to the first input terminal of the DPGA and
configuring the programmable buffer coupled to the first input terminal of the DPGA to operate linearly for voltage provided to the first input terminal of the DPGA provided by the transimpedance amplifier.

17. A method as claimed in claim 16, including configuring the programmable buffer coupled to the first input terminal of the DPGA to operate as one of at least a single-ended first-operating region operational amplifier, a single-ended second-operating region operational amplifier or a rail-to-rail operational amplifier.

18. An amplifier circuit for a glucose monitoring system, comprising:
a transimpedance amplifier including a first input terminal configured for coupling to a sensor for sensing an analyte, a second input terminal coupled to a voltage source, and an output terminal that provides an output based on a difference between first and second inputs on the first input terminal and the second input terminal; and
a differential programmable gain amplifier (DPGA) having a first input terminal coupled to the output of the output terminal of the transimpedance amplifier and a second input terminal coupled to a reference voltage source and that provides an output based on a difference between the first and second input terminals of the DPGA, the DPGA having a plurality of selectable operation ranges where each operation range of the plurality of selectable operation ranges has a different linearity region and wherein an operation range of the plurality of selectable operational ranges is selected responsive to a value of the output of the differential programmable gain amplifier;
the transimpedance amplifier and the DPGA are integrated together on a chip.

19. The amplifier circuit of claim 18, wherein the plurality of selectable operation ranges includes a single-ended first-operating region operational region, a single-ended second-operating region operational region, or a rail to rail operating region.

20. The amplifier circuit of claim 18, wherein the DPGA includes a first programmable buffer having the plurality of selectable operation ranges and a second programmable buffer having the plurality of selectable operation ranges, and wherein each of the first and second terminals of the DPGA are coupled, respectively, to the first programmable buffer and the second programmable buffer.

\* \* \* \* \*